US010006832B2

(12) United States Patent
Otsuki

(10) Patent No.: US 10,006,832 B2
(45) Date of Patent: Jun. 26, 2018

(54) EXHAUST GAS ANALYSIS SYSTEM MOUNTED ON MOBILE OBJECT

(71) Applicant: HORIBA, Ltd., Kyoto (JP)

(72) Inventor: Yoshinori Otsuki, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 146 days.

(21) Appl. No.: 14/923,851

(22) Filed: Oct. 27, 2015

(65) Prior Publication Data

US 2016/0116373 A1 Apr. 28, 2016

(30) Foreign Application Priority Data

Oct. 27, 2014 (JP) .................. 2014-218274

(51) Int. Cl.
*G01N 15/10* (2006.01)
*G01F 1/34* (2006.01)
(Continued)

(52) U.S. Cl.
CPC ............. *G01M 15/106* (2013.01); *G01F 1/34* (2013.01); *G01N 1/2252* (2013.01); *G01N 2001/2255* (2013.01)

(58) Field of Classification Search
CPC ....... G01M 15/106; G01F 1/34; G01N 1/2252
See application file for complete search history.

(56) References Cited

U.S. PATENT DOCUMENTS

2011/0120096 A1    5/2011  Nakamura
2012/0210697 A1*   8/2012  Garimella ............ F01N 3/208
                                                  60/274

(Continued)

FOREIGN PATENT DOCUMENTS

EP    2302354 A1    3/2011
EP    2515095 A1    10/2012
(Continued)

OTHER PUBLICATIONS

EESR dated Mar. 31, 2016 issued for European Patent Application No. 15 191 459.5, 10 pgs.
(Continued)

*Primary Examiner* — R. A. Smith
*Assistant Examiner* — John M Royston
(74) *Attorney, Agent, or Firm* — Brooks Kushman P.C.

(57) ABSTRACT

The present invention includes an exhaust gas flow channel that permits passage of an exhaust gas, a diluent gas flow channel that permits passage of a diluent gas, a main flow channel that permits passage of a diluted exhaust gas, a diluted exhaust gas flow rate measurement mechanism disposed on the main flow channel, and a diluent gas flow rate measurement mechanism disposed on the diluent gas flow channel. The diluted exhaust gas flow rate measurement mechanism and the diluent gas flow rate measurement mechanism each have a pressure sensor section. Furthermore, a pressure sensitive element of the pressure sensor section in the diluted exhaust gas flow rate measurement mechanism, and a pressure sensitive element of the pressure sensor section in the diluent gas flow rate measurement mechanism, are oriented in an identical direction in order to reduce an influence of acceleration in association with movement of a mobile object.

5 Claims, 4 Drawing Sheets

(51) Int. Cl.
    *G01N 1/22*    (2006.01)
    *G01M 15/10*   (2006.01)

(56) References Cited

U.S. PATENT DOCUMENTS

2012/0266687 A1* 10/2012 Takahashi ............ G01N 1/2252
                                                    73/861
2013/0014560 A1*  1/2013 Wei ..................... G01N 1/2252
                                                    73/23.31

FOREIGN PATENT DOCUMENTS

JP      2000-028499 A    1/2000
WO      2010007965 A1    1/2010

OTHER PUBLICATIONS

Yutaka Yamagishi et al., Tunnel Vision a Particulate Matter Sampling System Using a Partial Flow Dilution Method Has Been Designed to Perform Sampling during a Transient Test Cycle, Testing Technology International, Feb. 1, 2000, pp. 95-100.

* cited by examiner

EXHAUST GAS ANALYSIS SYSTEM MOUNTED ON MOBILE OBJECT

CROSS-REFERENCE TO RELATED APPLICATION

This application claims priority to JP Application No. 2014-218274, filed Oct. 27, 2014, the disclosure of which is incorporated in its entirety by reference herein.

BACKGROUND OF THE INVENTION

Field of the Invention

The present invention relates to an exhaust gas analysis system to be mounted on a mobile object, such as a vehicle. The exhaust gas analysis system collects part or all of an exhaust gas discharged from an internal combustion engine of the mobile object, and dilutes and analyzes the exhaust gas.

Description of the Related Art

A conventional exhaust gas analysis system mounted on a vehicle, is configured as described in WO 2010/007965. In this configuration, part of the exhaust gas discharged from the internal combustion engine is separately collected through an exhaust gas introduction pipe and introduced into a micro-tunnel (diluter). The collected exhaust gas is diluted with a diluent gas, and the diluted exhaust gas thus obtained is then introduced into an analyzer, such as a PM collection filter.

In the exhaust gas analysis system, a diluent gas flow rate regulation mechanism and a diluent gas flow rate measurement mechanism are disposed on the diluent gas introduction pipe connected to the micro-tunnel. A diluted exhaust gas flow rate regulation mechanism and a diluted exhaust gas flow rate measurement mechanism are disposed on a flow channel on a downstream side of the micro-tunnel. And, a differential pressure flowmeter, such as a Venturi flowmeter, is used for the diluent gas flow rate measurement mechanism and the diluted exhaust gas flow rate measurement mechanism.

The exhaust gas analysis system is configured to perform a partial-flow dilution control on the basis of a flow rate of the exhaust gas discharged from the internal combustion engine, by controlling the diluent gas flow rate regulation mechanism and the diluted exhaust gas flow rate regulation mechanism. That is, a flow rate of the diluent gas introduced into the micro-tunnel is regulated so as to stabilize a ratio (split ratio) of the flow rate of the exhaust gas discharged from the internal combustion engine and the flow rate of the exhaust gas separately collected into the exhaust gas introduction pipe.

However, in the exhaust gas analysis system mounted on the vehicle, acceleration can act on the exhaust gas analysis system, depending on operation situations, such as an acceleration operation, deceleration operation, or coasting operation of the vehicle, or road situations, such as road surface irregularities. Consequently, a measurement error caused by an influence of acceleration can occur on a differential pressure gauge of the diluent gas flow rate measurement mechanism (differential pressure flowmeter) and on a differential pressure gauge of the diluted exhaust gas flow rate measurement mechanism (differential pressure flowmeter). Here, the differential pressure gauge used for flow rate measurement handles micro pressures and hence is significantly affected by the acceleration. Therefore, the influence thereof differs depending on a direction in which the acceleration acts.

Particularly, in a system in which the flow rate of the exhaust gas, to be separately collected into the exhaust gas introduction pipe, is controlled to be a difference between the diluted exhaust gas flow rate and the diluent gas flow rate ("sample flow rate"="diluted exhaust gas flow rate"−"diluent gas flow rate"), a control error of the sample flow rate may increase due to a measurement error of the diluted exhaust gas flow rate and a measurement error of the diluent gas flow rate.

SUMMARY OF THE INVENTION

Problems to be Solved by the Invention

Accordingly, the present invention has been made to solve the above problems, and a major object thereof is to reduce the influence of acceleration that acts on a differential pressure sensor section in association with movement of the mobile object.

Means for Solving the Problems

An exhaust gas analysis system according to the present invention is mounted on a mobile object with an internal combustion engine, and measures a target ingredient in an exhaust gas discharged from the internal combustion engine. The exhaust gas analysis system includes an exhaust gas flow channel that permits passage of the exhaust gas, a diluent gas flow channel that permits passage of a diluent gas to dilute the exhaust gas, a main flow channel that permits passage of a diluted exhaust gas being a mixture of the exhaust gas and the diluent gas, a diluted exhaust gas flow rate measurement mechanism that is disposed on the main flow channel and measures a flow rate of the diluted exhaust gas, and a diluent gas flow rate measurement mechanism that is disposed on the diluent gas flow channel and measures a flow rate of the diluent gas. The diluted exhaust gas flow rate measurement mechanism and the diluent gas flow rate measurement mechanism each include a pressure sensor section. A pressure sensitive element of the pressure sensor section in the diluted exhaust gas flow rate measurement mechanism and a pressure sensitive element of the pressure sensor section in the diluent gas flow rate measurement mechanism are oriented in an identical direction in order to reduce an influence of acceleration in association with movement of the mobile object.

Because the pressure sensitive element in the diluted exhaust gas flow rate measurement mechanism and the pressure sensitive element in the diluent gas flow rate measurement mechanism are oriented in the identical direction, acceleration acts in an identical direction on the pressure sensitive element in the diluted exhaust gas flow rate measurement mechanism and the pressure sensitive element in the diluent gas flow rate measurement mechanism. Consequently, a measurement error in the diluted exhaust gas flow rate measurement mechanism may occur due to the influence of acceleration and a measurement error in the diluent gas flow rate measurement mechanism and/or due to the influence of acceleration can be made equal or approximately equal to each other. Therefore, in a system where control is made so that a flow rate of the exhaust gas, separately collected into the exhaust gas flow channel, corresponds to a difference between a diluted exhaust gas flow rate and a diluent gas flow rate ("sample flow rate"="diluted exhaust gas flow rate"−"diluent gas flow rate"), the measurement error of the diluted exhaust gas flow rate and the measurement error of the diluent gas flow rate can be cancelled out against each other to reduce the influence of acceleration on the sample flow rate.

And, when the errors are accumulated at a maximum level, a sample flow rate is as follows:

Sample flow rate=(diluted exhaust gas flow rate+e1)−(diluted air flow rate−e2)

wherein, e1 is a measurement error of a diluted exhaust gas flow rate due to acceleration, and e2 is a measurement error of a diluent gas flow rate due to acceleration.

When the measurement errors of the two flow rates are cancelled out by the configuration of the present invention, a sample flow rate is as follows:

Sample flow rate=(diluted exhaust gas flow rate+e1)−(diluted air flow rate+e2)

Therefore, when e1=e2, the errors are reduced to zero.

The exhaust gas analysis system further includes a diluted exhaust gas collection flow channel that is connected to the main flow channel and collects part of the diluted exhaust gas from the main flow channel, and a collection flow rate measurement mechanism that is disposed on the diluted exhaust gas collection flow channel and measures a flow rate of a diluted exhaust gas passing through the diluted exhaust gas collection flow channel. The collection flow rate measurement mechanism includes a pressure sensor section. The pressure sensitive element of the pressure sensor section in the diluted exhaust gas flow rate measurement mechanism, the pressure sensitive element of the pressure sensor section in the diluent gas flow rate measurement mechanism, and a pressure sensitive element of the pressure sensitive section in the collection flow rate measurement mechanism are oriented in an identical direction in order to reduce the influence of acceleration in association with the movement of the mobile object.

Thus, the pressure sensitive elements in all of the flow rate measurement mechanisms are oriented in the identical direction, and hence the measurement errors of the flow rate due to the acceleration can be made equal or approximately equal to each other. Therefore, the influence of acceleration on the sample flow rates can be further reduced by cancelling out the measurement errors of the flow rates.

This configuration makes it possible to reduce the influence of acceleration on the sample flow rate in an exhaust gas analysis system obtainable by combining a PM collection using the PM collection filter, and a continuous measurement of particle size concentration, or the like, using an analyzer, such as a diffusion charge sensor (DCS).

Preferably, the pressure sensitive elements in the flow rate measurement mechanisms have a flat plate shape being deformable under pressure, and the pressure sensitive elements are oriented in an identical plane direction.

The flat plate-shaped pressure sensitive elements in the flow rate measurement mechanisms make it easy to dispose the pressure sensitive elements in the identical direction. Alternatively, the plane directions of the pressure sensitive elements may be oriented in a horizontal direction. This makes it possible to reduce the influence of their own weight on the measurement.

The pressure sensor sections in the flow rate measurement mechanisms preferably have an identical configuration.

Owing to the pressure sensor sections having the identical configuration, the pressure sensitive elements in the flow rate measurement mechanisms are subjected to the same influence of acceleration, thereby still further reducing the influence of acceleration on the sample flow rate.

Specifically, the pressure sensor sections of the flow rate measurement mechanisms preferably each have a differential pressure sensor, and the pressure sensitive elements of the differential pressure sensors in the flow rate measurement mechanisms are preferably oriented in an identical direction. And, the pressure sensitive elements of the differential pressure sensor sections are to detect a pressure difference between an upstream pressure and a downstream pressure, and are deformable under the upstream pressure and the downstream pressure. The pressure sensitive elements may receive the upstream pressure and the downstream pressure by a single member at the same time, or may be divided into an element to receive the upstream pressure and an element to receive the downstream pressure.

Preferably, the pressure sensor sections in the flow rate measurement mechanisms each have an absolute pressure sensor, and the pressure sensitive elements of the absolute pressure sensors in the flow rate measurement mechanisms are oriented in an identical direction.

Preferably, the pressure sensor section in flow rate measurement mechanism each have a differential pressure sensor and an absolute pressure sensor, and the pressure sensitive elements of the differential pressure sensors in the flow rate measurement mechanisms are oriented in an identical direction, and the pressure sensitive elements of the absolute pressure sensors in the flow rate measurement mechanisms are oriented in the same direction as the pressure sensitive elements of the differential pressure sensors in order to further reduce the influence of acceleration on the sample flow rate.

Effects of the Invention

According to the present invention thus configured, the pressure sensitive elements in the flow rate measurement mechanisms are oriented in the identical direction, making it possible to reduce the influence of acceleration exerted on the pressure sensor sections in association with the movement of the mobile object.

MODE FOR CARRYING OUT THE INVENTION

An embodiment of an exhaust gas analysis system according to the present invention is described below with reference to the drawings.

The exhaust gas analysis system 100 of the present embodiment is mounted on an automobile, such as a passenger car or a motor truck, and measures a mass concentration of particulate matter (PM) contained in an exhaust gas discharged from an internal combustion engine, namely, the engine during the time that the automobile travels on a road.

Figure 1:
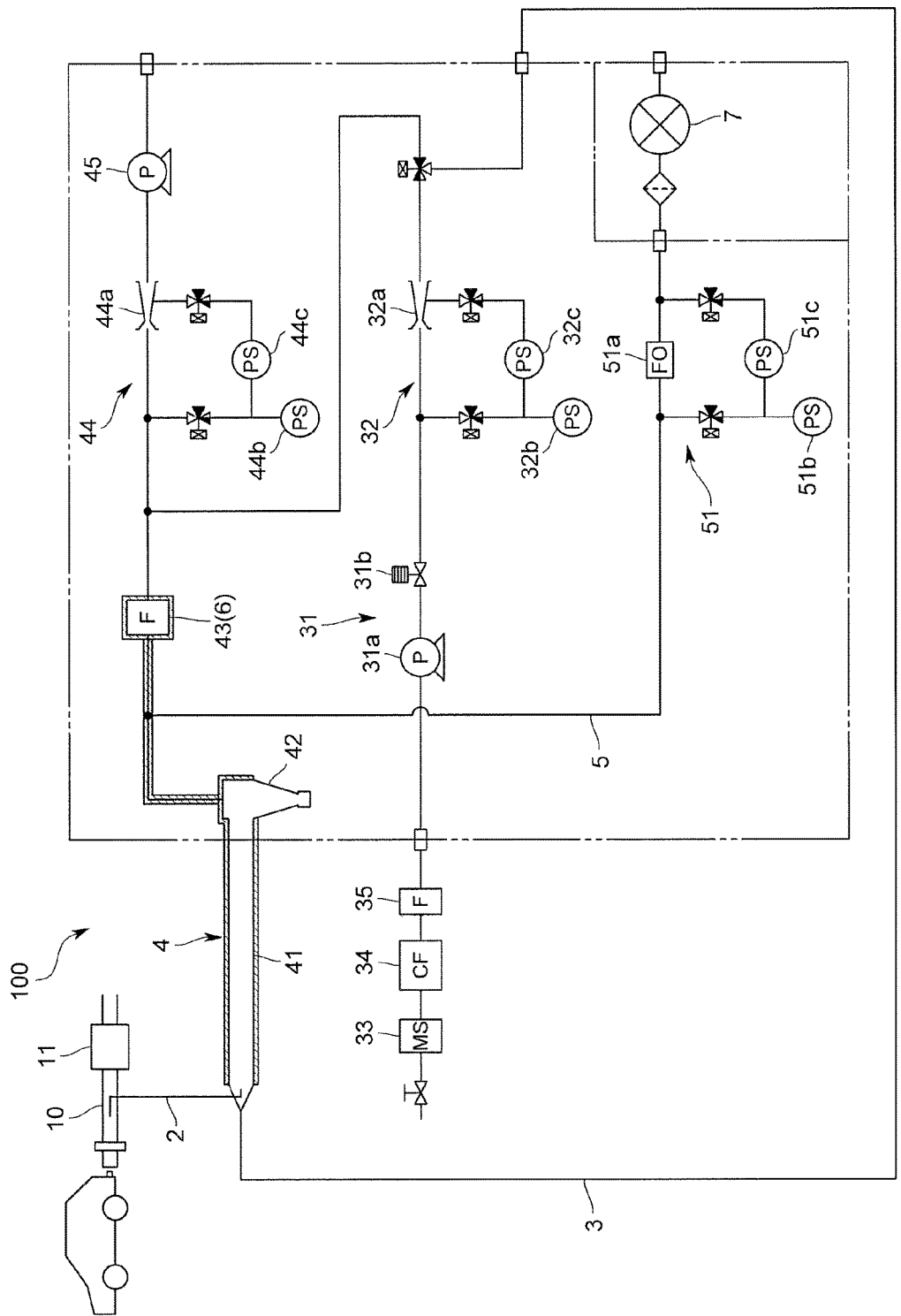
FIG. 1 is a schematic diagram showing a configuration of an exhaust gas analysis system of an embodiment.

Specifically, as shown in FIG. 1, the exhaust gas analysis system 100 collects part of the exhaust gas passing through an exhaust gas pipe connected to the engine, and dilutes and analyzes the exhaust gas. The exhaust gas analysis system 100 includes an exhaust gas flow channel 2 that permits passage of the exhaust gas, a diluent gas flow channel 3 that permits passage of a diluent gas, a main flow channel 4 that has the exhaust gas flow channel 2 and the diluent gas flow channel 3 connected thereto and that permits passage of a diluted exhaust gas being a mixture of the exhaust gas and the diluent gas, and a diluted exhaust gas collection flow channel 5 to collect part of the diluted exhaust gas from the main flow channel 4.

The flow channels 2 to 5, and corresponding instruments disposed on the flow channels 2 to 5 are described below.

The exhaust gas flow channel 2 is to separately collect part of the exhaust gas passing through an exhaust pipe or an attachment pipe 10 overlying an opening of the exhaust pipe, and is to introduce the collected exhaust gas into the main flow channel 4 without being diluted. One end of the exhaust gas flow channel 2 communicates with an inside of the exhaust pipe or the attachment pipe 10, and the other end is connected to the main flow channel 4. Neither a measuring instrument to measure an exhaust gas flow rate nor a control instrument to control the exhaust gas flow rate is disposed on the exhaust gas flow channel 2 of the present embodiment.

Figure 2:
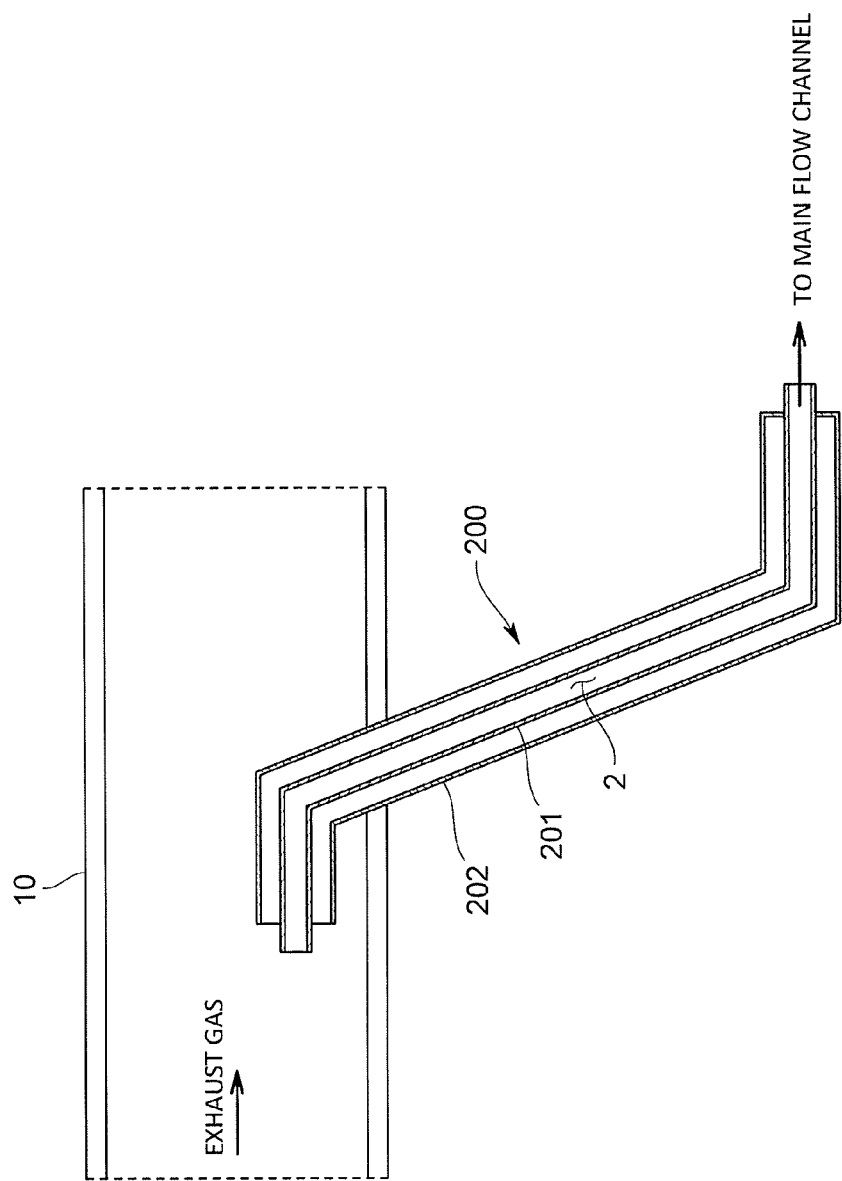
FIG. 2 is a schematic diagram showing a configuration of an exhaust gas flow channel of the embodiment.

Specifically, as shown in FIG. 2, the exhaust gas flow channel 2 is made up of an exhaust gas introduction pipe 20 having a double pipe structure. The exhaust gas introduction pipe 200 has an inner pipe 201 that permits passage of an exhaust gas to be separately collected, and an outer pipe 202 disposed outside the inner pipe 201. In one end of the exhaust gas introduction pipe 200 which communicates with the inside of the exhaust pipe or the attachment pipe 10, a gap between the inner pipe 201 and the outer pipe 202 is opened to introduce the exhaust gas into a space formed between the inner pipe 201 and the outer pipe 202. In the other end of the exhaust gas introduction pipe 200 which is connected to the main flow channel 4, the gap between the inner pipe 201 and the outer pipe 202 is closed.

In the exhaust gas introduction pipe 200 thus configured, the inner pipe 201 can be externally heated by the exhaust gas that enters into the space between the inner pipe 201 and the outer pipe 202, making it possible to relax a temperature difference between the partially collected exhaust gas and an inner wall surface of the inner pipe 201. It is therefore possible to configure an exhaust gas sampling system that minimizes particle loss in the exhaust gas introduction pipe 200. The effect thereof becomes further significant in one in which an exhaust gas temperature varies greatly, such as an exhaust gas test to analyze an exhaust gas by transiently changing operating conditions of the engine.

An exhaust gas flow rate sensor 11, such as a Pitot tube type flowmeter, which measures a flow rate of an exhaust gas passing through the exhaust pipe, is disposed on a downstream side of the opening at the one end of the exhaust gas flow channel 2.

The diluent gas flow channel 3 is to introduce the diluent gas for diluting the exhaust gas (atmospheric air in the present embodiment) into the main flow channel 4. One end of the diluent gas flow channel 3 is disposed at a position that permits intake of atmospheric air, and the other end is connected to the main flow channel 4. A diluent gas flow rate regulation mechanism 31 to regulate a flow rate of a diluent gas to be introduced into the main flow channel 4, and a diluent gas flow rate measurement mechanism 32 to measure a flow rate of the diluent gas are disposed on the diluent gas flow channel 3 in the order named from an upstream side.

A mist separator 33 to remove water contained in the atmospheric air, a filter 34, such as an activated carbon adsorption filter, to remove organic ingredients contained in the atmospheric air, and a filter 35, such as an HEPA filter, to remove dust contained in the atmospheric air are disposed on the upstream side of the diluent gas flow rate regulation mechanism 31 in the order named from the upstream side.

The diluent gas flow rate regulation mechanism 31 includes a supply pump 31a of, for example, diaphragm type, and a flow rate regulation valve 31b, such as a proportional solenoid valve, disposed on the upstream side or the downstream side of the supply pump 31a (which is disposed on the downstream side in the present embodiment). The diluent gas flow rate measurement mechanism 32 is a differential pressure flowmeter, and includes a venturi 32a, a pressure sensor 32b that is an absolute pressure sensor to measure an inlet pressure of the venturi 32a, and a differential pressure sensor 32c to measure a pressure difference between an inlet and a throat of the venturi 32a. Alternatively, a fluid resistor, such as an orifice, a flow nozzle, or a pitot tube, may be used instead of the venturi 32a.

On the basis of a diluent gas flow rate obtained by the diluent gas flow rate measurement mechanism 32 thus configured, a valve opening of the flow rate regulation valve 31b of the diluent gas flow rate regulation mechanism 31 is to be controlled by a control instrument (not shown), thereby controlling the flow rate of the exhaust gas introduced into the main flow rate 4.

The main flow channel 4 includes a diluter (micro-tunnel) 41, a dust remover of, for example, cyclone type 42, a filter placement part 43, a diluted exhaust gas flow rate measurement mechanism 44, and a diluted exhaust gas flow rate regulation mechanism 45. The diluter 41 has the exhaust gas flow channel 2 and the diluent gas flow channel 3 connected thereto, and mixes the exhaust gas and the diluent gas together. The dust remover 42 is disposed on the downstream side of the diluter 41 and removes dust in the diluted exhaust gas. The filter placement part 43 is disposed on the downstream side of the dust remover 42, and has a PM collection filter 6 that is a first analyzer placed thereon. The diluted exhaust gas flow rate measurement mechanism 44 is disposed on the downstream side of the filter placement part 43 (PM collection filter 6) and measures a flow rate of the diluted exhaust gas passing through the main flow channel 4. The diluted exhaust gas flow rate regulation mechanism 45 is disposed on the downstream side of the diluted exhaust gas flow rate regulation mechanism 44, and regulates a diluted exhaust gas flow rate. The diluter 41, the dust remover 42, the filter placement part 43, and the flow channel therebetween are heated to a predetermined temperature (for example, 47±5° C.) by a heater.

The diluted exhaust gas flow rate measurement mechanism 44 is a differential pressure flowmeter, and includes a venturi 44a, a pressure sensor 44b that is an absolute pressure sensor to measure an inlet pressure of the venturi 44a, and a differential pressure sensor 44c to measure a pressure difference between an inlet and a throat of the venturi 44a. Alternatively, a fluid resistor, such as an orifice, a flow nozzle, or a pitot tube, may be used instead of the venturi 44a.

The diluted exhaust gas flow rate regulation mechanism 45 is, for example, a diaphragm type suction pump, and a suction flow rate is changeable by controlling a rotational frequency thereof by a control instrument (not shown).

The diluted exhaust gas collection flow channel 5 is to collect and introduce part of the diluted exhaust gas from the main flow channel 4 into an analyzer 7 that is a second analyzer. The flow channel 5 includes a collection flow rate measurement mechanism 51 to measure a collection flow rate of the diluted exhaust gas passing through the diluted exhaust gas collection flow channel 5. In the present embodiment, the diluted exhaust gas is to be collected into the diluted exhaust gas collection flow channel 5 by a suction pump (not shown) disposed inside the analyzer 7. In addition to the analyzer 7, a suction pump may be disposed on the downstream side of the collection flow rate measurement mechanism 51. The analyzer 7 is to continuously measure particulate matter contained in the diluted exhaust gas, specifically, continuously measure physical properties that indirectly indicate a mass of the particulate matter, such as a surface area, a number, and a particle size distribution of the particulate matter. Examples of the analyzer of the present embodiment are a diffusion charge sensor (DCS), a hydrogen flame ionization detector (FID), a condensation particle counter (CPC), an electrical low pressure impactor (ELPI), and a scanning mobility particle sizer (SMPS).

The collection flow rate measurement mechanism 51 is a differential pressure flowmeter, and includes an orifice 51a, a pressure sensor 51b that is an absolute pressure sensor to measure a pressure on the upstream side of the orifice 51a, and a differential pressure sensor 51c to measure a pressure difference between the upstream side and the downstream side of the orifice 51a. Alternatively, a fluid resistor, such as a venturi, a flow nozzle, or a pitot tube, may be used instead of the orifice 51a.

The control instrument of the exhaust gas analysis system 100 controls in real time a flow rate of the diluent gas to be introduced into the diluter 41 (sample dilution control) so as to stabilize a ratio of a flow rate of the exhaust gas passing through the exhaust pipe obtained by the exhaust gas flow rate sensor 11, and a flow rate of the exhaust gas passing through the exhaust gas flow channel 2 (split ratio) by controlling the diluent gas flow rate regulation mechanism 31 and the diluted exhaust gas flow rate regulation mechanism 45.

Figure 3:
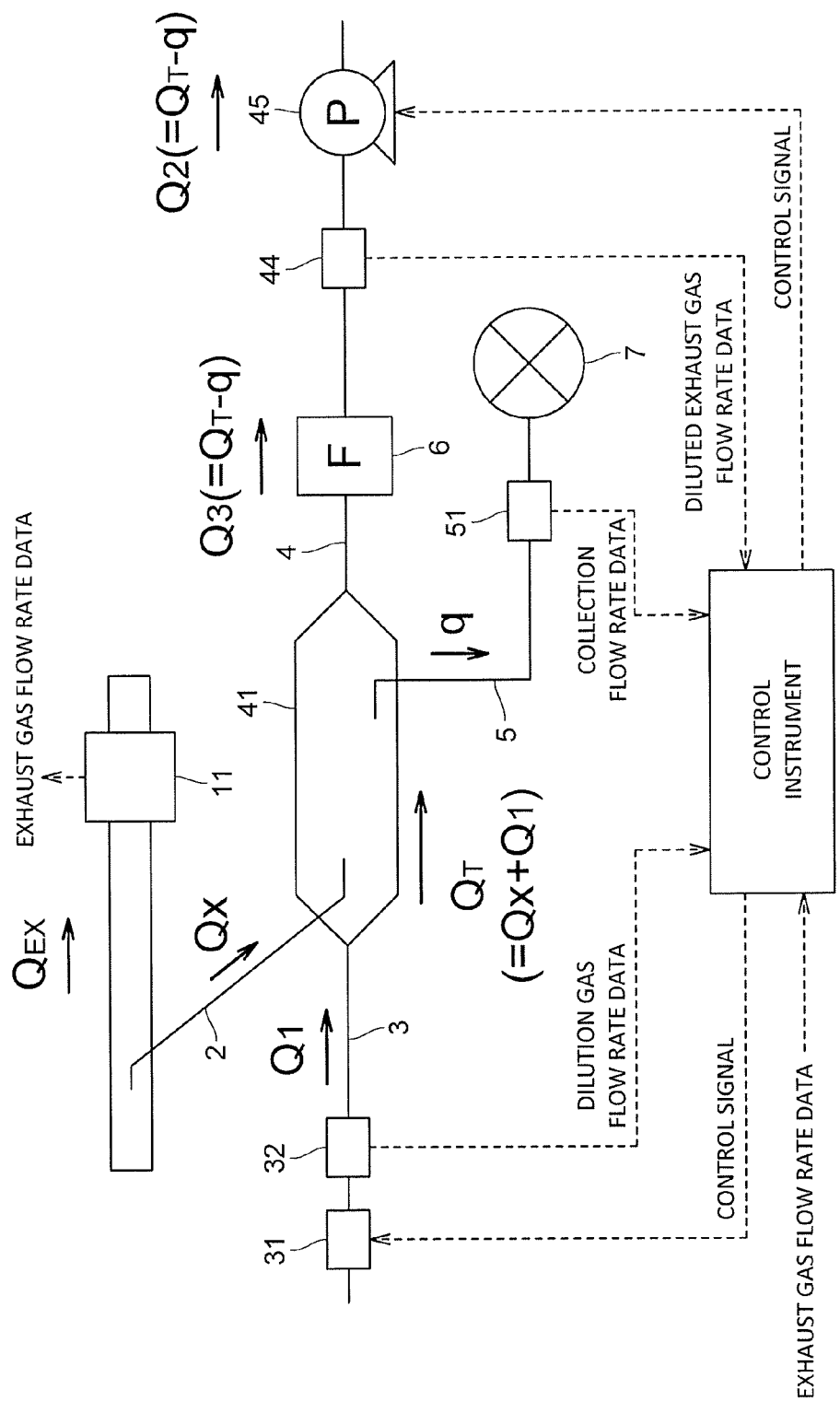
FIG. 3 is a schematic diagram showing flow rates in the flow channels.

Specifically, as shown in FIG. 3, the control instrument stabilizes a total flow rate $Q_T$ ($=Q_X+Q_1$) of a flow rate of the exhaust gas passing through the exhaust gas flow channel 2 (a sample flow rate) QX and a flow rate Q1 of the diluent gas passing through the diluent gas flow channel 3. The control instrument also increases or decreases the diluent gas flow rate $Q_1$ to ensure a fixed ratio of a flow rate $Q_{EX}$ of the exhaust gas passing through the exhaust pipe and the flow rate $Q_X$ of the sample flow passing through the exhaust gas flow channel 2. That is, the control instrument acquires exhaust gas flow rate data from the exhaust gas flow rate sensor 11, and inputs a control signal to the proportional solenoid valve 31b of the diluent gas flow rate regulation mechanism 31 on the basis of the exhaust gas flow rate data in order to increase or decrease the diluent gas flow rate $Q_1$.

The control instrument changes a setting flow rate $Q_2$ being set in the diluted exhaust gas flow rate regulation mechanism 45, depending on a collection flow rate q of the diluted exhaust gas passing through the diluted exhaust gas collection flow channel 5. That is, the control instrument acquires collection flow rate data from the collection flow rate measurement mechanism 51, and inputs a control signal to the diluted exhaust gas flow rate regulation mechanism 45 on the basis of the collection flow rate data in order to change the setting flow rate $Q_2$.

More specifically, the control instrument brings the setting flow rate $Q_2$ into a value ($Q_T$-q) obtained by subtracting the collection flow rate q from the total flow rate $Q_T$. Thus, the total flow rate $Q_T$ (namely, the diluted exhaust gas flow rate on the upstream side of the opening at one end of the diluted exhaust gas collection flow channel 5) can be maintained at a setting value to be determined by a desired split ratio, irrespective of the collection flow rate q of the diluted exhaust gas collection flow channel 5. Here, a flow rate $Q_3$ passing through the PM collection filter is a value ($Q_T$-q) obtainable by subtracting the collection flow rate q from the total flow rate $Q_T$.

The diluted exhaust gas flow rate regulation mechanism 45 of the present embodiment is a suction pump whose rotational frequency is variable. Therefore, the control instrument attains the setting flow rate $Q_2$ ($=Q_T$-q) by controlling the rotational frequency of the suction pump depending on the collection flow rate q of the diluted exhaust gas passing through the diluted exhaust gas collection flow channel 5.

The setting flow rate being set in the diluted exhaust gas flow rate regulation mechanism 45 is changed depending on the collection flow rate q of the diluted exhaust gas passing through the diluted exhaust gas collection flow channel 5. This makes it possible to avoid fluctuation in the total flow rate $Q_T$ of the flow rate of exhaust gas passing through the exhaust gas flow channel 2 and the flow rate of the diluent gas passing through the diluent gas flow channel 3 varies depending on the collection flow rate q, while eliminating the need of a correction gas flow channel having a compressed air source. This contributes to downsizing the exhaust gas analysis system while reducing an error in the partial-flow dilution control.

None of gases coming from the exterior (for example, conventional correction gas and atmospheric air) is mixed with the diluted exhaust gas after passing through the PM collection filter 6. It is therefore possible to measure, for example, a $CO_2$ concentration of the diluted exhaust gas by using the exhaust of the main flow channel 4 (specifically, on the downstream side of the diluted exhaust gas flow rate regulation mechanism 45), and thus it is easy to verify accuracy of a dilution ratio.

In the exhaust gas analysis system 100 of the present embodiment, the differential pressure sensor 32c of the diluent gas flow rate measurement mechanism 32, the differential pressure sensor 44c of the diluted exhaust gas flow rate measurement mechanism 44, and the differential pressure sensor 51c of the collection flow rate measurement mechanism 51 are the same differential pressure sensor. That is, the differential pressure sensor 32c, the differential pressure sensor 44c, and the differential pressure sensor 51c have the same configuration.

Figure 4:
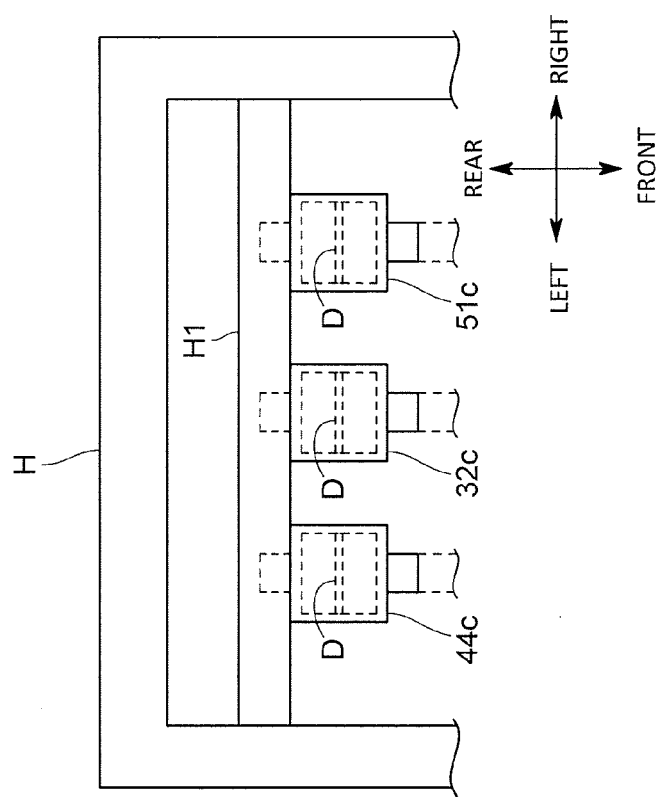
FIG. 4 is a schematic diagram showing a layout embodiment of differential pressure sensors in flow rate measurement mechanisms.

Specifically, as shown in FIG. 4, the differential pressure sensors 32c, 44c, and 51c have a flat plate shaped diaphragm D that is a pressure sensitive element. The differential pressure sensors 32c, 44c, and 51c have, on one surface of the diaphragm D, an upstream-side introduction passage (not shown) that permits introduction of an upstream-side fluid, and have, on the other surface of the diaphragm D, a downstream-side introduction passage (not shown) that permits introduction of a downstream-side fluid. Because the differential pressure sensors 32c, 44c, and 51c have the same configuration, the diaphragms D of the differential pressure sensors 32c, 44c, and 51c are identical in size, thickness, and material of a pressure receiving surface.

As a detection method for the differential pressure sensors 32c, 44c, and 51c, electrostatic capacity method, semiconductor strain gauge method, or vibration method is employable. The electrostatic capacity method is intended to detect displacement due to a differential pressure of the diaphragm in the form of electrostatic capacity. Semiconductor strain gauge method includes forming a semiconductor strain gauge by diffusing impurities on a silicon diaphragm, and detecting displacement due to a differential pressure of the diaphragm as a resistance change. The vibration method includes connecting a wire-shaped vibrator to a diaphragm, and detecting vibration of the vibrator corresponding to displacement due to a differential pressure of the diaphragm.

As shown in FIG. 4, the diaphragm D of the differential pressure sensor 32c, the diaphragm D of the differential pressure sensor 44c, and the diaphragm D of the differential pressure sensor 51c are oriented in an identical direction in order to reduce the influence of acceleration in association with the automobile traveling on a road. That is, the diaphragms D of the differential pressure sensors 32c, 44c, and 51c are disposed parallel to one another. In the present embodiment, the diaphragms D of the differential pressure sensors 32c, 44c, and 51c are disposed with their planar direction oriented in a horizontal direction so that each of the differential pressure sensors 32c, 44c, and 51c is insusceptible to the influence of a weight of the diaphragm D itself. The differential pressure sensors 32c, 44c, and 51c have the same configuration, and hence are disposed so that the differential pressure sensors 32c, 44c, and 51c have the same attachment posture.

The differential pressure sensors 32c, 44c, and 51c are housed in a single housing H, and are secured to a common member H1 constituting the housing H. The housing H accommodates piping constituting the flow channels 2 to 5, and various kinds of instruments disposed on the flow channels 2 to 5.

According to the exhaust gas analysis system 100 thus configured, all of the diaphragms D of the differential pressure sensors 32c, 44c, and 51c in the flow rate measurement mechanisms 32, 44, and 51 are oriented in the identical direction. Therefore, acceleration is to act in an identical direction on all of the diaphragms D of the differential pressure sensors 32c, 44c, and 51c during the time that the automobile travels on the road. Consequently, a measurement error of the diluent gas flow rate $Q_1$ due to the influence of the acceleration, a measurement error of the diluted exhaust gas flow rate $Q_2$ (=$Q_T$–q) due to the influence of the acceleration, and a measurement error of the collection flow rate q due to the influence of the acceleration can be made equal or approximately equal to one another. Therefore, when the flow rate $Q_x$ of the exhaust gas that is separately collected into the exhaust gas flow channel 2 is controlled to correspond to a difference between the diluted exhaust gas flow rate $Q_2$ and the diluent gas flow rate $Q_1$, namely, (sample flow rate)=(diluted exhaust gas flow rate)–(diluent gas flow rate), it is possible to reduce the influence of the acceleration on the sample flow rate by cancelling out the measurement error of the diluted exhaust gas flow rate $Q_2$ and the measurement error of the diluent gas flow rate $Q_1$. Further in the present embodiment, because the setting flow rate of the suction pump as being the diluted exhaust gas flow rate regulation mechanism 45 is set to $Q_T$–q, the error of the partial-flow dilution control can be further reduced by cancelling out the measurement error of the collection flow rate q and the measurement error of the diluted exhaust gas flow rate $Q_2$.

The present invention is not limited to the foregoing embodiment.

For example, the foregoing embodiment is configured to change the setting flow rate $Q_2$ being set in the diluted exhaust gas flow rate regulation mechanism 45 depending on the collection flow rate q of the diluted exhaust gas passing through the diluted exhaust gas collection flow channel 5. Instead of this configuration, a correction gas flow channel may be disposed for returning a correction gas. Specifically, in order to return the correction gas (for example, air) having the same flow rate as the collection flow rate q that is obtained from the diluted exhaust gas collection flow channel 5 to the downstream side of the PM collection filter, a correction gas introduction flow channel is connected between the PM collection filter and a suction pump disposed on the downstream side of the PM collection filter. The correction gas introduction flow channel is provided with a mass flow controller to control the correction gas flow rate to the same flow rate as the collection flow rate. In this configuration, the setting flow rate $Q_2$ being set in the diluted exhaust gas flow rate regulation mechanism 45 is to be a total flow rate $Q_T$ (=$Q_X$–$Q_1$) of a flow rate of the exhaust gas passing through the exhaust gas flow channel 2 (a sample flow rate) $Q_X$ and a flow rate $Q_1$ of the diluent gas passing through the diluent gas flow channel 3.

In the foregoing embodiment, the pressure sensitive elements of the differential pressure sensors disposed on all of the flow channels, specifically, the differential pressure sensor of the diluted exhaust gas flow rate measurement mechanism, the differential pressure sensor of the diluent gas flow rate measurement mechanism, and the differential pressure sensor of the collection flow rate measurement mechanism are oriented in the identical direction; however it may be configured that at least two of the differential pressure sensors are oriented in an identical direction. Particularly, in the partial-flow dilution control, the pressure sensitive element of the differential pressure sensor of the diluted exhaust gas flow rate measurement mechanism and the pressure sensitive element of the differential pressure sensor of the diluent gas flow rate measurement mechanism are preferably oriented in an identical direction.

Although the differential pressure sensor section of the flow rate measurement mechanism in the foregoing embodiment is made up of the single differential pressure sensor, it may be made up of a pressure sensor to measure an upstream pressure and a pressure sensor to measure a downstream pressure.

Furthermore, the diaphragm of the absolute pressure sensor 32b, the diaphragm of the absolute pressure sensor 44b, and the diaphragm of the absolute pressure sensor 51b in the foregoing embodiment may be oriented in an identical direction in order to reduce the influence of acceleration in association with the automobile traveling on the road. This makes it possible to also cancel out the influence of acceleration on the upstream-side pressure sensor, thereby further reducing the influence of acceleration on the sample flow rate.

The pressure sensitive elements of the absolute pressure sensors 32b, 44b, and 51b, and the pressure sensitive elements of the differential pressure sensors 32c, 44c, and 51c may be oriented in an identical direction. This makes it possible to also cancel out the influence of acceleration on the upstream-side pressure sensor in addition to the differential pressure sensors, thereby further reducing the influence of acceleration on the sample flow rate.

The foregoing embodiment is configured to perform proportional dilution control under which the diluent gas flow rate is controlled with respect to the flow rate of the engine exhaust gas passing through the exhaust pipe so that the exhaust gas is divided at a fixed ratio and introduced into the main flow channel. Alternatively, it may be configured to perform fixed dilution control under which the diluent gas flow rate is controlled so that a ratio of the flow rate of the exhaust gas divided from the exhaust pipe and the diluent gas flow rate is fixed, namely, a dilution ratio is fixed.

Furthermore, the exhaust gas analysis system of the foregoing embodiment may collect part or all of the exhaust gas discharged from the automobile engine mounted on a chassis dynamometer, and may dilute and analyze the exhaust gas.

Although the foregoing embodiment is configured to analyze the exhaust gas from the internal combustion engine mounted on the automobile, it may be configured to analyze an exhaust gas discharged from an internal combustion engine mounted on a mobile object, such as aircrafts and ships.

Although the foregoing embodiment is configured to separately collect part of the exhaust gas discharged from the internal combustion engine, it may be configured to collect all of the exhaust gas and then dilute and analyze the collected exhaust gas.

The present invention is not limited to the foregoing embodiment, and, of course, various kinds of modifications can be made therein without departing from the scope and gist of the present invention.

What is claimed is:

1. An exhaust gas analysis system being configured to be mounted on a mobile object with an internal combustion engine, and configured to measure a target ingredient in an exhaust gas discharged from the internal combustion engine, the exhaust gas analysis system comprising:
    an exhaust gas flow channel that permits passage of the exhaust gas;
    a diluent gas flow channel that permits passage of a diluent gas to dilute the exhaust gas;
    a main flow channel that permits passage of a diluted exhaust gas being a mixture of the exhaust gas and the diluent gas;
    a diluted exhaust gas flow rate measurement mechanism that is disposed on the main flow channel and measures a flow rate of the diluted exhaust gas; and
    a diluent gas flow rate measurement mechanism that is disposed on the diluent gas flow channel and measures a flow rate of the diluent gas,
    wherein the diluted exhaust gas flow rate measurement mechanism and the diluent gas flow rate measurement mechanism each have a pressure sensor section,
    wherein the pressure sensor sections each have a differential pressure sensor and an absolute pressure sensor,
    wherein pressure sensitive elements of the differential pressure sensors are oriented in an identical direction in order to reduce an influence of acceleration in association with movement of the mobile object, and
    wherein pressure sensitive elements of the absolute pressure sensors are oriented in an identical direction in order to reduce an influence of acceleration in association with movement of the mobile object.

2. The exhaust gas analysis system according to claim 1, further comprising:
    a diluted exhaust gas collection flow channel that is connected to the main flow channel and collects part of the diluted exhaust gas from the main flow channel; and
    a collection flow rate measurement mechanism that is disposed on the diluted exhaust gas collection flow channel and measures a flow rate of the diluted exhaust gas passing through the diluted exhaust gas collection flow channel,
    wherein the collection flow rate measurement mechanism comprises a pressure sensor section having a pressure sensitive element oriented in a direction identical to the pressure sensitive elements of the differential pressure sensors or the pressure sensitive elements of the absolute pressure sensors.

3. The exhaust gas analysis system according to claim 1, wherein
    the pressure sensitive elements are configured to have a flat plate shape being deformable under pressure.

4. The exhaust gas analysis system according to claim 1, wherein the pressure sensor sections have identical configuration.

5. An exhaust gas analysis method comprising:
    by an exhaust gas analysis system configured to be mounted on a mobile object with an internal combustion engine to measure a target ingredient in an exhaust gas discharged from the internal combustion engine, and including an exhaust gas flow channel, a diluent gas flow channel, a main flow channel, a diluted exhaust gas flow rate measurement mechanism that is disposed on the main flow channel, and a diluent gas flow rate measurement mechanism that is disposed on the diluent gas flow channel,
    permitting passage of the exhaust gas via the exhaust gas flow channel;
    permitting passage of a diluent gas via the diluent gas flow channel to dilute the exhaust gas;
    permitting passage of a diluted exhaust gas being a mixture of the exhaust gas and the diluent gas via the main flow channel;
    measuring a flow rate of the diluted exhaust gas via the diluted exhaust gas flow rate measurement mechanism; and
    measuring a flow rate of the diluent gas via the diluent gas flow rate measurement mechanism,
    wherein the diluted exhaust gas flow rate measurement mechanism and the diluent gas flow rate measurement mechanism each have a pressure sensor section,
    wherein the pressure sensor sections each have a differential pressure sensor and an absolute pressure sensor,
    wherein pressure sensitive elements of the differential pressure sensors are oriented in an identical direction in order to reduce an influence of acceleration in association with movement of the mobile object, and
    wherein pressure sensitive elements of the absolute pressure sensors are oriented in an identical direction in order to reduce an influence of acceleration in association with movement of the mobile object.

* * * * *